(12) United States Patent
Park

(10) Patent No.: US 11,710,552 B2
(45) Date of Patent: Jul. 25, 2023

(54) METHOD AND SYSTEM FOR REFINING LABEL INFORMATION

(71) Applicant: LUNIT INC., Seoul (KR)

(72) Inventor: Chunseong Park, Seoul (KR)

(73) Assignee: LUNIT INC., Seoul (KR)

(*) Notice: Subject to any disclaimer, the term of this patent is extended or adjusted under 35 U.S.C. 154(b) by 292 days.

(21) Appl. No.: 16/953,693

(22) Filed: Nov. 20, 2020

(65) Prior Publication Data
US 2021/0366594 A1    Nov. 25, 2021

(30) Foreign Application Priority Data

May 22, 2020 (KR) .......................... 10-2020-0061582

(51) Int. Cl.
*G16H 30/40* (2018.01)
*G06T 7/11* (2017.01)
*G06N 3/08* (2023.01)
*G06T 7/00* (2017.01)

(52) U.S. Cl.
CPC ............... *G16H 30/40* (2018.01); *G06N 3/08* (2013.01); *G06T 7/0012* (2013.01); *G06T 7/11* (2017.01); *G06T 2207/10056* (2013.01); *G06T 2207/20081* (2013.01); *G06T 2207/20084* (2013.01); *G06T 2207/30024* (2013.01)

(58) Field of Classification Search
CPC ......... G16H 30/40; G06T 7/11; G06T 7/0012; G06T 2207/10056; G06T 2207/20081; G06T 2207/20084; G06T 2207/30024; G06N 3/08
See application file for complete search history.

(56) References Cited

U.S. PATENT DOCUMENTS

| 7,471,815 | B2* | 12/2008 | Hong | ................... | G06T 7/0012 |
| | | | | | 382/128 |
| 2005/0074834 | A1* | 4/2005 | Chaplen | ............ | G01N 15/1475 |
| | | | | | 702/19 |
| 2016/0140749 | A1* | 5/2016 | Erhard | ................... | G06T 15/08 |
| | | | | | 345/424 |
| 2016/0335478 | A1* | 11/2016 | Bredno | ................ | G06T 7/0012 |
| 2018/0137119 | A1* | 5/2018 | Li | ........................ | G06F 16/5866 |
| 2020/0126207 | A1* | 4/2020 | Saltz | ....................... | G06K 9/628 |
| 2020/0388029 | A1* | 12/2020 | Saltz | ....................... | G06T 7/143 |
| 2021/0045716 | A1* | 2/2021 | Shiran | ..................... | G06N 20/00 |
| 2021/0074425 | A1* | 3/2021 | Carter | .................. | G06F 18/217 |
| 2021/0233642 | A1* | 7/2021 | Sue | ........................ | G16H 30/40 |
| 2022/0036575 | A1* | 2/2022 | Shin | ....................... | A61B 5/201 |
| 2022/0222815 | A1* | 7/2022 | Zeineh | ................. | G06K 9/6254 |

FOREIGN PATENT DOCUMENTS

| JP | 2019521443 A | 7/2019 |
| KR | 1020200054138 A | 5/2020 |

\* cited by examiner

*Primary Examiner* — Vu Le
*Assistant Examiner* — Julius Chai
(74) *Attorney, Agent, or Firm* — Sughrue Mion, PLLC

(57) ABSTRACT

A method for refining label information, which is performed by at least one computing device is disclosed. The method includes acquiring a pathology slide image including a plurality of patches, inferring a plurality of label information items for the plurality of patches included in the acquired pathology slide image using a machine learning model, applying the inferred plurality of label information items to the pathology slide image, and providing the pathology slide image applied with the inferred plurality of label information items to an annotator terminal.

18 Claims, 12 Drawing Sheets
(4 of 12 Drawing Sheet(s) Filed in Color)

METHOD AND SYSTEM FOR REFINING LABEL INFORMATION

CROSS-REFERENCE TO RELATED APPLICATIONS

This application claims priority to Korean Patent Application No. 10-2020-0061582 filed on May 22, 2020, the entire contents of which are herein incorporated by reference.

TECHNICAL FIELD

The present disclosure relates to a method for providing refinement for label information. More specifically, the present disclosure provides a method and a system capable of inferring label information on target data using a machine learning model, and determining data to be used for training the machine learning model based on a response to the inferred label information item.

BACKGROUND ART

In recent years, as hardware such as processors, memories, and cameras are fast developed, artificial intelligence (AI) technology has been developed and is receiving increasing attention. For example, researches on applying these AI technologies to the field of image processing is being actively conducted. In particular, the AI technology is being used in the field of automatic generation and analysis of the labels of pathology slide images for tissue samples.

Meanwhile, supervised learning is a machine learning method for constructing an artificial neural network model for performing inference on input data by learning a dataset tagged with label information. Annotation task for tagging label information to generate a training dataset is generally carried out by humans, and most annotation tasks are time-consuming and expensive, and it may be difficult to maintain consistency during annotation tasks. For example, the annotation tasks by the experienced practitioners are necessary for the training data of an artificial neural network model for diagnosing the type or location of a lesion in the pathology slide image. However, it is close to impossible for even a skilled practitioner to read a pathology slide containing millions of cells without error and with consistency.

Meanwhile, in the process of generating training data of an artificial neural network model in order to automatically generate labels of target data (e.g., conventional pathology slide images), it can be time-consuming and expensive since it requires experienced experts to perform the annotation tasks for the entire target data (e.g., the entire pathology slide images), which may be inefficient. In addition, semi-supervised learning in which label information is extracted and re-learned using a machine learning prediction model can be used, but tasks that can directly utilize the predictive model may be limited. For example, the predictive model can be used when label information is a classification problem (for example, a problem with one correct answer), but when label information is a segmentation problem, it may be difficult to expect performance improvement.

SUMMARY

Some embodiments of the present disclosure provide a method for refining label information for target data to solve the problems described above.

The method and system according to some embodiments of the present disclosure may determine a patch to be refined, based on at least one of a confidence score or an entropy value for each of a plurality of patches.

The method and system according to some embodiments of the present disclosure may provide a visual representation of at least one patch according to label information inferred using a machine learning model.

The method and system according to some embodiments of the present disclosure may assign a training weight to label information refined by an annotator.

The present disclosure may be implemented in various ways, including a method, a system, or a computer-readable storage medium storing instructions, and a computer program.

According to an exemplary embodiment, a method for refining label information may includes acquiring a pathology slide image including a plurality of patches, inferring a plurality of label information items for the plurality of patches included in the acquired pathology slide image using a machine learning model, applying the inferred plurality of label information items to the pathology slide image, and providing the pathology slide image applied with the inferred plurality of label information items to an annotator terminal.

According to an embodiment, the method may further include receiving, from the annotator terminal, a response to at least one label information item among the plurality of inferred label information items. In an example, at least one label information item may be associated with at least one of the plurality of patches.

According to an embodiment, the receiving, from the annotator terminal, the response to at least one label information item among the inferred plurality of label information items may include, when receiving a confirmation on the at least one label information item, classifying the at least one patch and the at least one label information item into a training dataset of the machine learning model.

According to an embodiment, the receiving, from the annotator terminal, the response to at least one label information item among the inferred plurality of label information items may include receiving a refined label information item for the at least one patch, and classifying the at least one patch and the refined label information item into a training dataset of the machine learning model.

According to an embodiment, the classifying the at least one patch and the refined label information item into the training dataset of the machine learning model may include assigning a weight to the refined label information item for the at least one patch, which is used for training the machine learning model.

According to an embodiment, the providing the pathology slide image applied with the inferred plurality of label information items to the annotator terminal may include providing a compressed image of the pathology slide image to an annotator terminal, and the receiving the refined label information item for the at least one patch may include: receiving from the annotator terminal a request for the at least one label information item corresponding to a first compressed label information item selected from the compressed image, providing the at least one label information item to the annotator terminal, and receiving a refined label information item for the at least one label information item provided. In an example, the compressed image may be associated with a compressed label information item of a plurality of label information items.

According to an embodiment, the inferring a plurality of label information items for the plurality of patches included in the acquired pathology slide image using the machine learning model may include calculating at least one of a confidence score or an entropy value for each of the plurality of patches, and determining at least one first patch to be refined from among the plurality of patches based on at least one of the calculated confidence score or the entropy value.

According to an embodiment, the applying the inferred plurality of label information items to the pathology slide image may include outputting a visual representation of the determined at least one first patch to be refined.

According to an embodiment, the plurality of label information items for the plurality of patches may include a plurality of classes associated with the plurality of patches, and the calculating at least one of the confidence score or the entropy value for each of the plurality of patches may include assigning a weight to the entropy value for a target class among the plurality of classes associated with the plurality of patches.

According to an embodiment, the determining at least one patch to be refined from among the plurality of patches may include determining, from among the plurality of patches, at least one second patch to be refined, which is associated with the target class having the weighted entropy value, and the applying the inferred plurality of label information items to the pathology slide image includes outputting a visual representation of the determined at least one second patch to be refined.

According to yet another embodiment, there are included a memory storing one or more instructions, and a processor configured to, by executing of the stored one or more instructions, acquire a pathology slide image including a plurality of patches; infer a plurality of label information items for the plurality of patches included in the acquired pathology slide image using a machine learning model, apply the inferred plurality of label information items to the pathology slide image, and provide the pathology slide image applied with the inferred plurality of label information items to an annotator terminal.

According to some embodiments of the present disclosure, data for training an artificial neural network may be efficiently generated by semi-automatically performing a labor-intensive data annotation process.

According to some embodiments of the present disclosure, a hard negative mining technique can be easily implemented by determining that the machine learning model has low confidence and assigning a training weight to label information refined by an annotator. Accordingly, a training dataset for a problem that is difficult for the machine learning model to infer may be generated.

According to some embodiments, by providing a visual representation for a plurality of patches according to label information inferred using a machine learning model, there is an effect that the label information can be selectively refined. Accordingly, the annotator can reduce the time and cost of generating the label information since it is possible to refine the label information by checking the area where the machine learning model is determined to be uncertain.

The effects of the present disclosure are not limited to the effects described above, and other effects not described will be able to be clearly understood by those of ordinary skill in the art (hereinafter, referred to as "ordinary technician") from the description of the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure will be described with reference to the accompanying drawings described below, where similar reference numerals indicate similar components, but not limited thereto, in which.

DETAILED DESCRIPTION OF THE INVENTION

Figure 1:
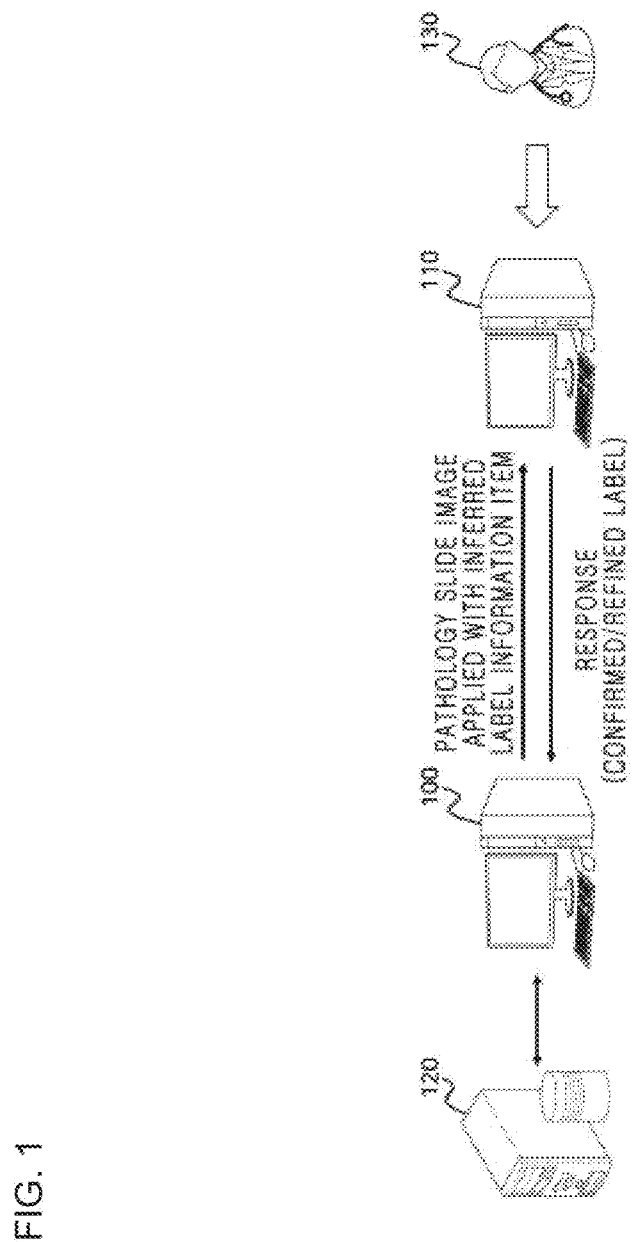
FIG. 1 is an exemplary configuration diagram illustrating a system for refining label information according to an exemplary embodiment.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding components are assigned the same reference numerals. In addition, in the following description of the embodiments, duplicate descriptions of the same or corresponding components may be omitted. However, even if descriptions of components are omitted, it is not intended that such components are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. In addition, in a specific case, a term is arbitrarily selected by the applicant, and the meaning of the term will be described in detail in a corresponding description of the embodiments. Therefore, the terms used in the present disclosure should be defined based on the meaning of the terms and the overall contents of the present disclosure rather than a simple name of each of the terms.

As used herein, the singular forms 'a,' 'an,' and 'the' are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to execute at least one processor. Accordingly, as an example, the "module" or "unit" may include components such as software components, object-oriented software components, class components, and task components, and at least one of processes, functions, attributes, procedures, subroutines, program code segments of program code, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

According to an embodiment of the present disclosure, the "module" or "unit" may be implemented as a processor and a memory. A "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination of processing devices, e.g., a combination of a DSP and a microprocessor, a plurality of microprocessors, one or more microprocessors in conjunction with a DSP core, or any other combination of such configurations. In addition, the "memory" should be interpreted broadly to encompass any electronic component capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory that is integral to a processor is in electronic communication with the processor.

In the present disclosure, the "system" may refer to at least one of a server device and a cloud device, but not limited thereto. For example, the system may include one or more server devices. As another example, the system may include one or more cloud devices. As another example, the system may be configured with both a server device and a cloud device and operated.

In the present disclosure, the "target data" may refer to any data or data item that can be used for training a machine learning model, and may include, for example, data representing an image, data representing voice or voice characteristics, and data representing specific information (information associated with manufacturing, distribution, logistics, finance, strategy/utilities, services, education, automobiles, games, public industries and services, marketing/advertising, healthcare, media/communications, consumer goods, and the like), but is not limited thereto. In the present disclosure, the whole pathology slide image and/or a plurality of patches included in the pathology slide image are explained as the target data, but is not limited thereto, and any data that can be used for training a machine learning model may correspond to the target data. In addition, the target data may be tagged with label information through an annotation task.

In the present disclosure, the "pathology slide image" refers to an image obtained by capturing a pathological slide fixed and stained through a series of chemical treatments in order to observe a tissue removed from a human body with a microscope. In an example, the pathology slide image may refer to a whole slide image including a high-resolution image of the entire slide. For example, the pathology slide image may refer to a digital image captured with a microscope, and may include information on cells, tissues, and/or structures in the human body. Further, the pathology slide image may include one or more patches, and the label information may be applied (e.g., tagged) to one or more patches through the annotation task.

In the present disclosure, the "patch" may refer to a small area within the pathology slide image. For example, the patch may include an area corresponding to a semantic object extracted by performing segmentation on the pathology slide image. As another example, the patch may refer to a combination of pixels associated with the label information generated by analyzing the pathology slide image.

In the present disclosure, the "machine learning model" may include any model that is used to infer an answer to a given input. According to an embodiment, the machine learning model may include an artificial neural network model including an input layer (layer), a plurality of hidden layers, and output layers. In an example, each layer may include one or more nodes. For example, the machine learning model may be trained to infer label information for the pathology slide image and/or at least one patch included in the pathology slide image. In this case, the label information generated through the annotation task may be used to train the machine learning model. In addition, the machine learning model may include weights associated with a plurality of nodes included in the machine learning model. In an example, the weight may include an any parameter associated with the machine learning model. In the present disclosure, the machine learning model may refer to an artificial neural network model, and the artificial neural network model may refer to the machine learning model.

In the present disclosure, "training" may refer to an any process of changing a weight included in the machine learning model by using at least one patch and the label information. According to an embodiment, the training may refer to a process of changing or updating weights associated with the machine learning model through one or more of forward propagation and backward propagation of the machine learning model using at least one patch and the label information.

In the present disclosure, the "label information" is correct answer information of the data sample information, which is acquired as a result of the annotation task. In addition, the label information may refer to the label information on at least one patch included in the pathology slide image, which is inferred through the machine learning model. The label may be used interchangeably with terms such as annotation, tag, and so on as used in the art. In an example, the label information may include information on a class for at least one patch and confidence and/or entropy value for the class.

In the present disclosure, the "class" may refer to classified information about cells, tissues, and/or structure in the patch. For example, when the cells in the patch correspond to lymphocytes, the class for the patch may refer to the class corresponding to the lymphocytes.

In the present disclosure, the "confidence score" may refer to a numerical value that represents the confidence of a label information item for each of a plurality of patches included in the pathology slide image. For example, the confidence score may include a confidence value for each of the one or more classes inferred to correspond to one patch.

In the present disclosure, the "entropy value" may refer to a numerical value that represents the uncertainty of a label information item for each of a plurality of patches included in the pathology slide image. According to an embodiment, the entropy value may be determined according to distribution of the confidence scores for each of one or more classes inferred to correspond to one patch. For example, when the confidence scores of a plurality of classes are evenly distributed, the entropy value may be high. In contrast, when the confidence score of one class is significantly higher than that of other classes, the entropy value may be low. In an example, the entropy value may be calculated for each class associated with the confidence score.

In the present disclosure, the "information item" may refer to information, and the information may refer to the information item.

In the present disclosure, "annotation" refers to a task of tagging label information to a data sample, or to tagged information (that is, annotation) itself. The annotation may be used interchangeably with terms such as tagging, labeling, and so on as used in the art.

In the present disclosure, "similar" may encompass sameness and similarity. For example, the similarity of two pieces of information may refer to that the two pieces of information are the same as or similar to each other.

In the present disclosure, "instruction" refers to a set of instructions grouped on the basis of a function, which is a component of a computer program and executed by a processor.

FIG. 1 is an exemplary configuration diagram illustrating a system for refining label information according to an exemplary embodiment. As shown, the system for refining a label information item may include an information processing system 100, an annotator terminal 110, and a storage system 120. In an example, the information processing system 100 may be configured to be connected communicatively to each of the annotator terminal 110 and the storage system 120. In FIG. 1, one annotator terminal 110 is shown, but the present disclosure is not limited thereto, and a plurality of annotator terminals 110 may be configured to be connected communicatively to the information processing system 100. In addition, the information processing system 100 is shown as one computing device in FIG. 1, but is not limited thereto, and the information processing system 100 may be configured to process information and/or data in a distributed manner through a plurality of computing devices. In addition, the storage system 120 is shown as a single device in FIG. 1, but is not limited thereto, and may be configured with a plurality of storage devices or a system supporting a cloud. In addition, in FIG. 1, each component of a system for refining a label information item represents functional elements that are functionally classified, and a plurality of components may be implemented in a form of integrating with each other in an actual physical environment.

The information processing system 100 and the annotator terminal 110 are any computing devices used to generate or infer label information for target data (e.g., at least one patch included in the pathology slide image) and refine label information. In an example, the computing device may refer to any type of device equipped with a computing function, and may be a notebook, a desktop, a laptop, a server, a cloud system, and the like, for example, but is not limited thereto.

The annotator terminal 110 may receive, from the information processing system 100, the target data (e.g., pathology slide image, at least one patch included in the pathology slide image, and the like) and the inferred label information, and may perform a response to the received image and label information. According to an embodiment, the annotator terminal 110 may receive confirmation on the target data from the annotator 130. For example, the confirmation on the target data may refer to confirmation on a label information item for at least one patch. The confirmation on the label information item for the target data may be provided to the information processing system 100. According to another embodiment, the annotator 130 may perform the annotation task on the target data (e.g., at least one patch in the received pathology slide image). The label information refined through such an annotation task may be provided to the information processing system 100 together with the corresponding target data (e.g., patch).

The information processing system 100 may classify the confirmed label information and the refined label information received from the annotator terminal 110 into a training dataset of a machine learning model and store it in the storage system 120. According to an embodiment, the information processing system 100 may use at least one patch associated with the received confirmation and/or the refined label information for the training of the machine learning model. In an example, since the refined label information is the label information that the annotator 130 directly worked on for a problem that is difficult for the machine learning model to infer, it may be helpful to improve the performance of the machine learning model. Accordingly, when training the machine learning model, the refined label information item for the target data (e.g., at least one patch) is assigned a weight, according to which the machine learning model may have a maximized performance improvement.

The storage system 120 is a device or a cloud system that stores and manages various data associated with the machine learning model for inferring label information. For efficient data management, the storage system 120 may use a database to store and manage various types of data. In an example, the various data may include any data associated with the machine learning model, and may include, as the target data, a file of a pathology slide image, metadata (e.g., image format, associated disease name, associated tissues, associated patient information, and the like) of a pathology slide image, data on an annotation task, data on an annotator, label information as a result of an annotation task, machine learning model, and the like, for example, but is not limited thereto. In FIG. 1, the information processing system 100 and the storage system 120 are shown as separate systems, but are not limited thereto, and may be integrated into one system.

Figure 2:
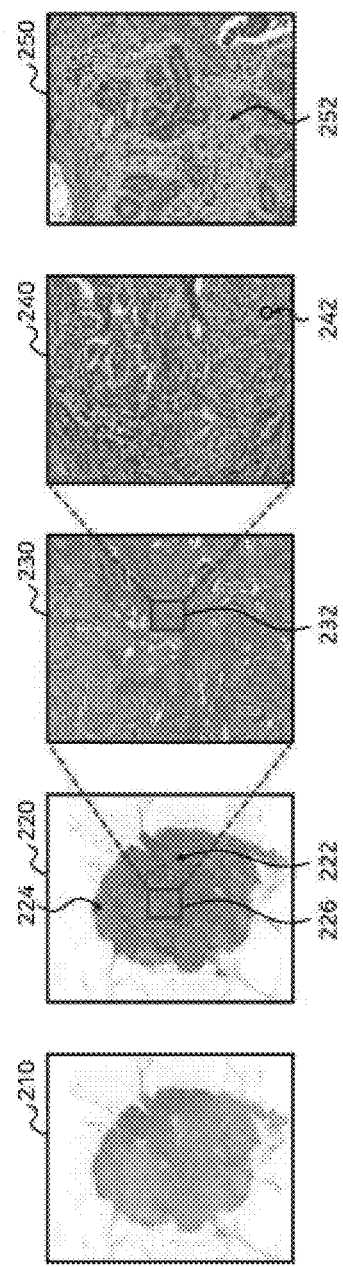
FIG. 2 is an exemplary diagram illustrating target data, which is a pathology slide image and at least one patch included in the pathology slide image according to an exemplary embodiment.

FIG. 2 is an exemplary diagram illustrating target data, which is a pathology slide image and at least one patch included in the pathology slide image according to an exemplary embodiment. As shown, the pathology slide image 210 may refer to a digital image generated by photographing a pathological slide stained and/or fixed through a series of chemical treatments of at least a part of the tissue obtained from the human body through a microscope and a camera. In FIG. 2, the pathology slide image 210 is shown as being stained by hematoxylin and eosin (H&E) staining technique, but is not limited thereto, and may include an image generated by photographing a pathological slide stained with a different already known staining technique through a microscope and a camera.

The pathology slide image 220 may include a plurality of label information items for a plurality of patches included in the image. According to an embodiment, the label information item may be generated by performing the annotation task for at least one patch by a person (e.g., the annotator 130). According to another embodiment, the information processing system (e.g., the information processing system 100) analyzes (e.g., infers) the pathology slide image 210 using the machine learning model, thus generating a plurality of label information items for a plurality of patches included in the pathology slide image.

The label information may include information for distinguishing an object included in the pathology slide and/or the patch in order to determine pathology. The pathology slide image 220 may include label information for a specific area. According to an embodiment, in the pathology slide image 220, a first area 222 may be tagged with the cancer stroma label information, and a second area 224 may be tagged with the cancer epithelium label information. For example, as shown, the first area 222 corresponding to the cancer stroma area is colored purple, and the second area 224 corresponding to the cancer epithelium area is colored sky blue, but is not limited thereto, and the label information may be expressed in various visual representations such as areas, figures, different colors, or texts. In addition, all or at least part of the colored area may correspond to one or more patches.

The information processing system may provide an enlarged image of at least a certain area (e.g., a patch) of the pathology slide image 220 in response to a request from the annotator terminal. According to an embodiment, the annotator terminal may select the certain area in the pathology slide image 220 as a first patch 226 by an input through the annotator. In response to this, the annotator terminal may acquire an enlarged image 230 for the first patch 226 from the information processing system. For example, the pathology slide image 220 may be provided in a compressed form of an original image captured with a microscope, and when a certain area of the compressed image is selected as a patch, the decompressed image corresponding to the patch may be provided to the annotator through the annotator terminal. Likewise, an enlarged image 240 of the second patch 232 included in the image 230 corresponding to the first patch may be acquired. In FIG. 2, the image 230 corresponding to the first patch 226 and the image 240 corresponding to the second patch 232 are enlarged at a specific magnification, but are not limited thereto, and the pathology slide image and/or the image corresponding to the patch included therein may be enlarged or reduced at various magnifications.

In an embodiment, lymphocytes 242 may be tagged as the label information to the patches in the pathology slide image. When the pathology slide image 220 is enlarged at a magnification similar to that of the second patch 232, the lymphocytes 242 included in the pathological slide (e.g., helper T cells, killer T cells, natural killer T cells, memory T cells, suppressor T cells and B cells, etc.) may be identified, but are not limited thereto, and the information processing system 100 may provide a visual representation on a low magnification image in an area corresponding to the specific label information. Further, in addition to the lymphocytes 242, the label information may include various cells included in the object of the pathological slide, such as neutrophils, eosinophils, basophils, monocytes, red blood cells, platelets, or the like.

The pathology slide image 250 may include label information for a specific area. According to an embodiment, a third area 252 in the pathology slide image 250 may be tagged with the label information indicating it to be an uncertain area. For example, as shown, in the label information inferred by the machine learning model of the information processing system 100, the third area 252 corresponding to the uncertain area is displayed in green, but is not limited thereto, and the label information may be expressed in various visual representations such as areas, figures, different colors, or texts. In addition, all or at least part of the colored area may correspond to one or more patches.

Figure 3:
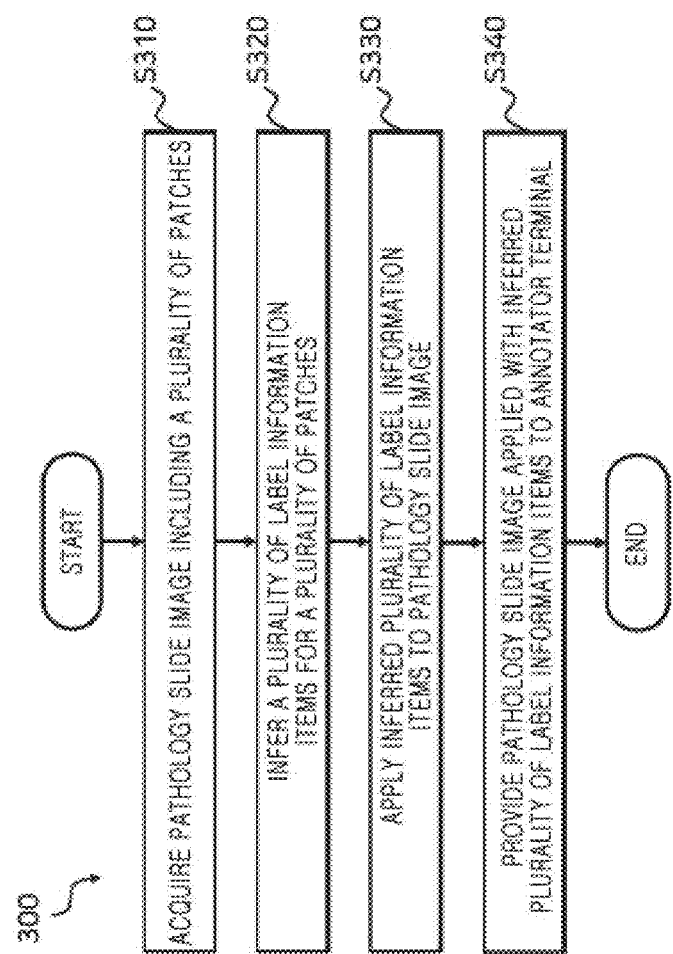
FIG. 3 is an exemplary flowchart illustrating a method for refining a label information item according to an exemplary embodiment.

FIG. 3 is an exemplary flowchart illustrating a method for refining a label information item according to an exemplary embodiment. According to an embodiment, the method 300 for refining label information may be performed by the information processing system (e.g., information processing system 100). Additionally or alternatively, the method 300 may be performed by the annotator terminal (e.g., annotator terminal 110). As shown, the method 300 may be initiated at S310 of acquiring a pathology slide image including a plurality of patches.

Then, at S320, a plurality of label information items for a plurality of patches may be inferred. For example, the pathology slide image including a plurality of patches acquired at S310 may be input to the machine learning model to extract label information items for a plurality of patches.

Next, at S330, the inferred plurality of label information items may be applied to the pathology slide image. For example, the information processing system may associate the plurality of label information items inferred at S320 with the pathology slide image including a plurality of patches acquired at S310.

Finally, at S340, the pathology slide image applied with the inferred plurality of label information items may be provided to the annotator terminal. The plurality of label information items included in the pathology slide image provided as described above may be identified by the annotator, and at least some information items may be refined.

Figure 4:
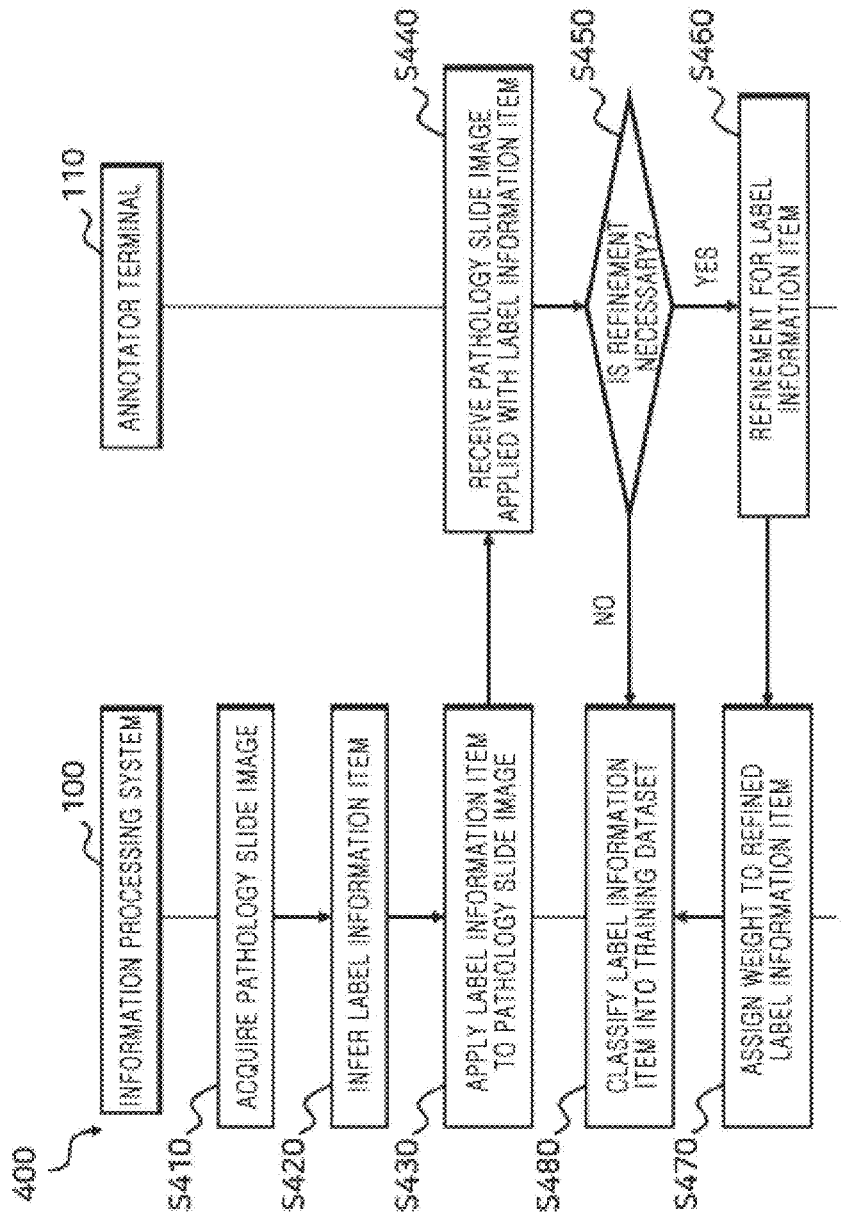
FIG. 4 is an exemplary flowchart illustrating a method for classifying a label information item into a training dataset according to an exemplary embodiment.

FIG. 4 is an exemplary flowchart illustrating a method for classifying a label information item into a training dataset according to an exemplary embodiment. The method 400 for classifying the label information into the training dataset may be performed by the information processing system 100. At this time, the information processing system 100 may be configured to communicate with the annotator terminal 110 in order to perform the method 400. As shown, the method 400 for classifying the label information into the training dataset may be initiated at S410 in which the information processing system 100 acquires a pathology slide image including a plurality of patches.

At S420, the information processing system 100 may infer the label information items for a plurality of patches included in the acquired pathology slide image using the machine learning model. For example, the pathology slide image including a plurality of patches acquired at S410 may be input to the machine learning model to extract label information items for a plurality of patches.

Next, at S430, the information processing system 100 may apply the inferred label information item to the pathology slide image. For example, the information processing system may tag a plurality of label information items inferred at S420 to the pathology slide image including a plurality of patches acquired at S410.

Next, at S440, the information processing system 100 may provide the pathology slide image applied with the inferred label information item to the annotator terminal 110. Then, at S450, the annotator terminal 110 may receive from the annotator (e.g., annotator 130) as to whether or not it is necessary to refine the label information input. In an embodiment, the information processing system 100 may receive from the annotator terminal 110 a response to at least one label information item from among the inferred plurality of label information items. In an example, at least one label information item may be associated with at least one of the plurality of patches.

When it is necessary to refine the label information item at S450, the annotator terminal 110 may receive the refined label information item from the annotator, at S460. For example, an annotator using the annotator terminal 110 may perform an annotation task of refining the label information item based on the pathology slide image applied with the label information item. Then, the label information item refined through the annotation task and at least one patch associated with the same may be provided to the information processing system 100.

At S470, the information processing system 100 may assign a weight to the label information item refined at S460. Accordingly, the refined label information item may have an increased importance as the training data when training a machine learning model. Then, moving to S480, the process may classify the refined label information item into a training dataset.

Alternatively, at S450, when it is not necessary to refine the label information item, the process may move to S480. In an embodiment, when receiving a confirmation on at least one label information item from the annotator terminal 110, the information processing system 100 may classify at least one patch and at least one label information item into the training dataset of the machine learning model.

Figure 5:
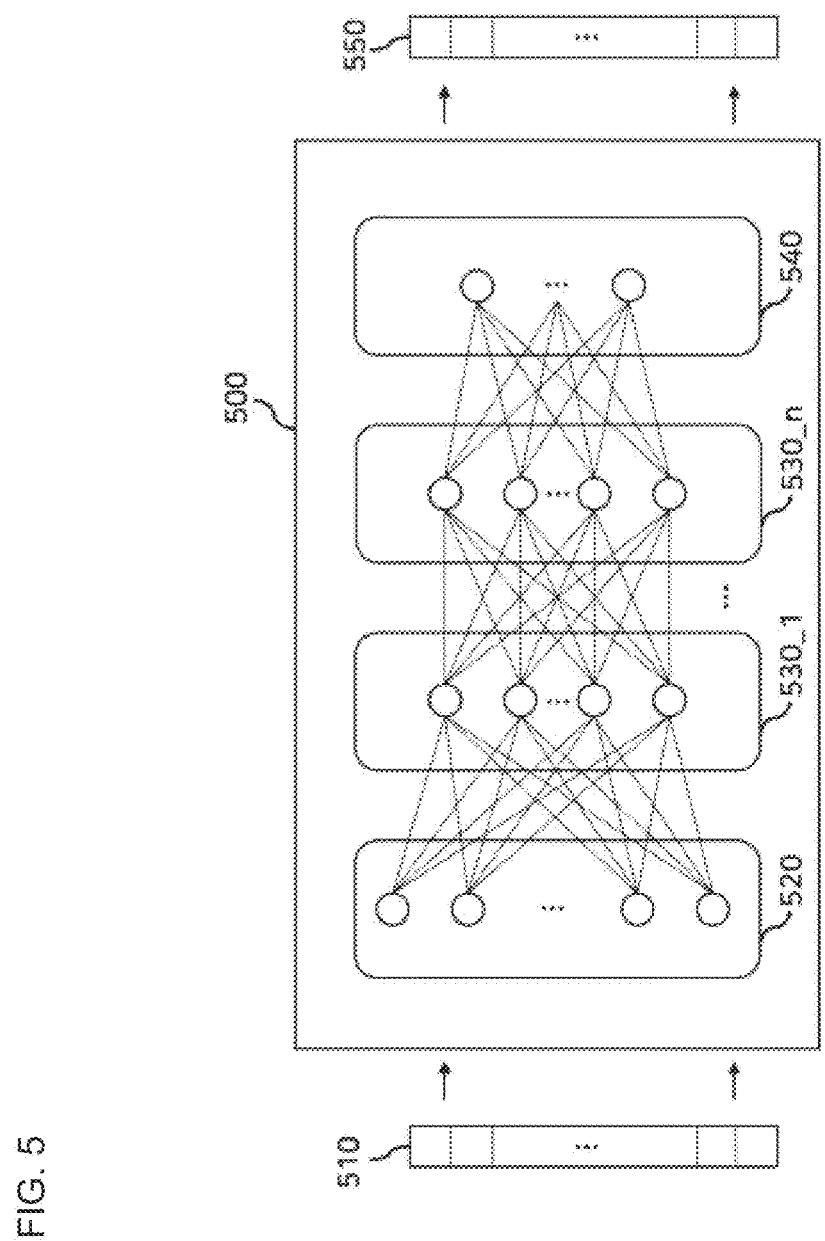
FIG. 5 is an exemplary diagram illustrating an artificial neural network model according to an exemplary embodiment.

FIG. 5 is an exemplary diagram illustrating an artificial neural network model according to an exemplary embodiment. In machine learning technology and cognitive science, an artificial neural network model 500 refers to a statistical training algorithm implemented based on a structure of a biological neural network, or to a structure that executes such algorithm.

According to an embodiment, the artificial neural network model 500 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 500 may include any probability model, neural network model, and the like, that is used in artificial intelligence learning methods such as machine learning and deep learning.

According to an embodiment, the artificial neural network model 500 may include an artificial neural network model configured for inputting a pathology slide image or at least one patch included in the pathology slide image and output label information. In this case, when inferring a label information item for at least one patch using the artificial neural network model 500, a confidence score and/or an entropy value for the label information item may be calculated. The calculated confidence score or entropy value may be used to determine a patch to be refined among a plurality of patches.

The artificial neural network model 500 is implemented as a multilayer perceptron (MLP) formed of multiple nodes and connections between them. The artificial neural network model 500 according to an embodiment may be implemented using one of various artificial neural network model structures including the MLP. As shown in FIG. 5, the artificial neural network model 500 includes an input layer 520 receiving an input signal or data 510 from the outside, an output layer 540 outputting an output signal or data 550 corresponding to the input data, and (n) number of hidden layers 530_1 to 530_n (where n is a positive integer) positioned between the input layer 520 and the output layer 540 to receive a signal from the input layer 520, extract the features, and transmit the features to the output layer 540. In an example, the output layer 540 receives signals from the hidden layers 530_1 to 530_n and outputs them to the outside.

The training method of the artificial neural network model 500 includes a supervised learning that trains for optimization for solving a problem with inputs of teacher signals (correct answer), and an unsupervised learning that does not require a teacher signal. In order to output the pathology slide image or the label information item for the patch using the learning pathology slide image or at least one patch included in the pathology slide image, the information processing system may analyze the input image using the supervised learning and then train the artificial neural network model 500 so that the label information item corresponding to the image can be inferred. In this case, the information processing system may receive the refined label information item for the pathology slide image or the at least one patch included in the pathology slide image from the annotator, and perform the supervised learning of the machine learning model using at least one patch and the refined label information item.

The artificial neural network model 500 trained as described above may be stored in the storage system (e.g., storage system 120), and output the label information item in response to an input of the pathology slide image or at least one patch included in a pathology slide image received from a communication interface and/or the annotator terminal (e.g., annotator terminal 110) or the storage system.

According to an embodiment, as shown in FIG. 5, an input variable of the artificial neural network model 500 capable of extracting the label information item may be the pathology slide image or at least one patch included in the pathology slide image. For example, the input variable input to the input layer 520 of the artificial neural network model 500 may be an image vector 510 that is the training image configured as one vector data element. In response to an input of the training image including at least a part of the pathology slide image, an output variable output from the output layer 540 of the artificial neural network model 500 may be a vector 550 representing or characterizing the label information item. For example, this label information item may include a class for at least a part of the pathology slide image. In addition, the output layer 540 of the artificial neural network model 500 may be configured to output a vector representing the confidence and/or the accuracy of the output label information item (e.g., class). For example, a vector representing confidence or accuracy for such an output can be interpreted or represented as a score. In the present disclosure, the output variable of the artificial neural network model 500 is not limited to the types described above, and may include any information/data representing the label information. The confidence score for each class can be used to calculate an entropy value that represents uncertainty for each class.

As described above, the input layer 520 and the output layer 540 of the artificial neural network model 500 are respectively matched with a plurality of output variables corresponding to a plurality of input variables, and the synaptic values between nodes included in the input layer 520, the hidden layers 530_1 to 530_n, and the output layer 540 are adjusted, so that by training, a correct output corresponding to a specific input can be extracted. Through this training process, the features hidden in the input variables of the artificial neural network model 500 may be confirmed, and the synaptic values (or weights) between the nodes of the artificial neural network model 500 may be adjusted so as to reduce the errors between the output variable calculated based on the input variable and the target output. Using the artificial neural network model 500 trained as described above, a label information item corresponding to the input image may be output in response to the input pathology slide image or at least one patch included in the pathology slide image.

Figure 6:
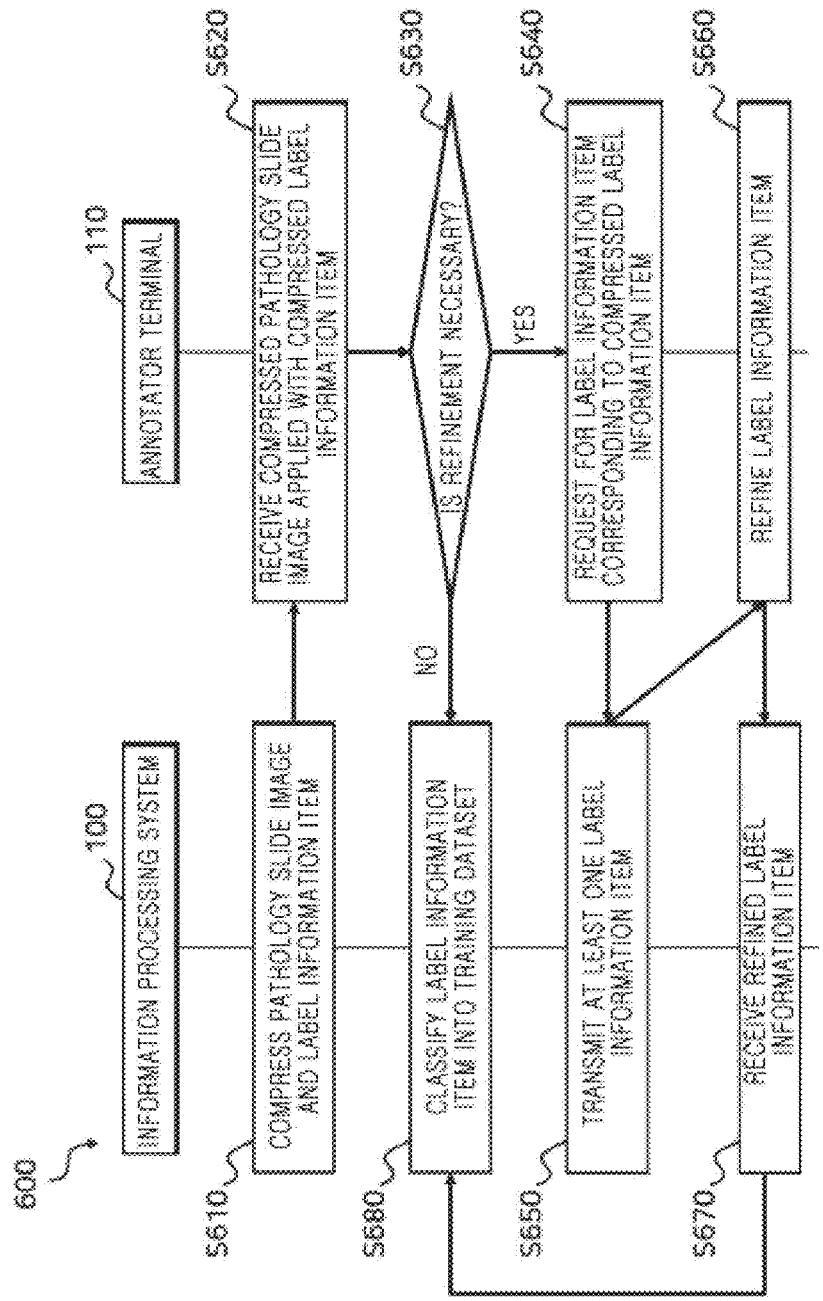
FIG. 6 is an exemplary flowchart illustrating a method for classifying a label information item into a training dataset according to an exemplary embodiment.

FIG. 6 is an exemplary flowchart illustrating a method for classifying a label information item into a training dataset according to an exemplary embodiment. The method 600 for classifying the label information item into the training dataset may be performed by the information processing system 100. At this time, the information processing system 100 may be configured to communicate with the annotator terminal 110 in order to perform the method 600. As shown, the method 600 for classifying the label information item into the training dataset may be initiated at S610 in which the information processing system 100 provides a compressed image of the pathology slide image to the annotator terminal 110. In an example, the compressed image may be associated with compressed label information items of a plurality of label information items. For example, since the resolution of the original uncompressed pathology slide image is considerably high, it may take a long time to transmit it to the annotator terminal 110. In addition, this high resolution of the original pathology slide image also requires the annotator to check a very large area corresponding to the original pathology slide image. In order to solve this problem, the information processing system 100 may transmit a compressed pathology slide image and a compressed label information item to the annotator terminal 110.

At S620, the information processing system 100 may provide the compressed pathology slide image applied with the compressed label information item to the annotator terminal 110.

Then, at S630, the annotator terminal 110 may receive from the annotator (e.g., annotator 130) as to whether or not it is necessary to refine the compressed label information item. In an embodiment, the information processing system 100 may receive from the annotator terminal 110 a response to at least one compressed label information item from among the plurality of compressed label information items.

If it is determined at S630 that refinement of the compressed label information item is necessary, the process may move to S640. At S640, the annotator terminal 110 may transmit to the information processing system 100 a request for at least one label information item corresponding to a first compressed label information item selected from the compressed image. For example, the annotator may check a portion that requires refinement by reviewing the compressed pathology slide image and the compressed label information item received through the annotator terminal 110. In addition, in order to refine the first compressed label information item determined by the annotator to be in need of refinement, the information processing system 100 may request an area in the pathology slide image of an original resolution corresponding to the first compressed label information item and at least one label information item in such area. In an example, the number of label information items included in the original area may be the same as or greater than the number of label information included in the compressed area.

Next, at S650, the information processing system 100 may provide at least one label information item to the annotator terminal 110. For example, in the transmitted compressed image, the information processing system 100 may transmit to the annotator terminal 110 an area in the associated pathology slide image of the original resolution which corresponds to the compressed label information item selected by the annotator terminal 110 and an original label information item included in such area.

At S660, the annotator terminal 110 may receive a refined label information item for at least one label information item included in the area of the original resolution from the annotator. Then, at S670, the information processing system 100 may receive a refined label information item for at least one label information item provided to the annotator terminal 110. When receiving the refined label information item, the process may move to S680, and the refined label information item and a patch associated therewith may be classified into the training dataset.

Alternatively, when it is determined at S630 that refinement of the label information item is not necessary, the process may move to S680. In an embodiment, when receiving a confirmation on at least one label information item for at least one patch from the annotator terminal 110, the information processing system 100 may classify at least one patch and at least one label information item into the training dataset of the machine learning model.

According to an embodiment, when rework of the label information is not necessary, the information processing system 100 may classify the corresponding label information into the training set of the machine learning model even without acquiring a confirmation through the annotator terminal 110.

Figure 7:
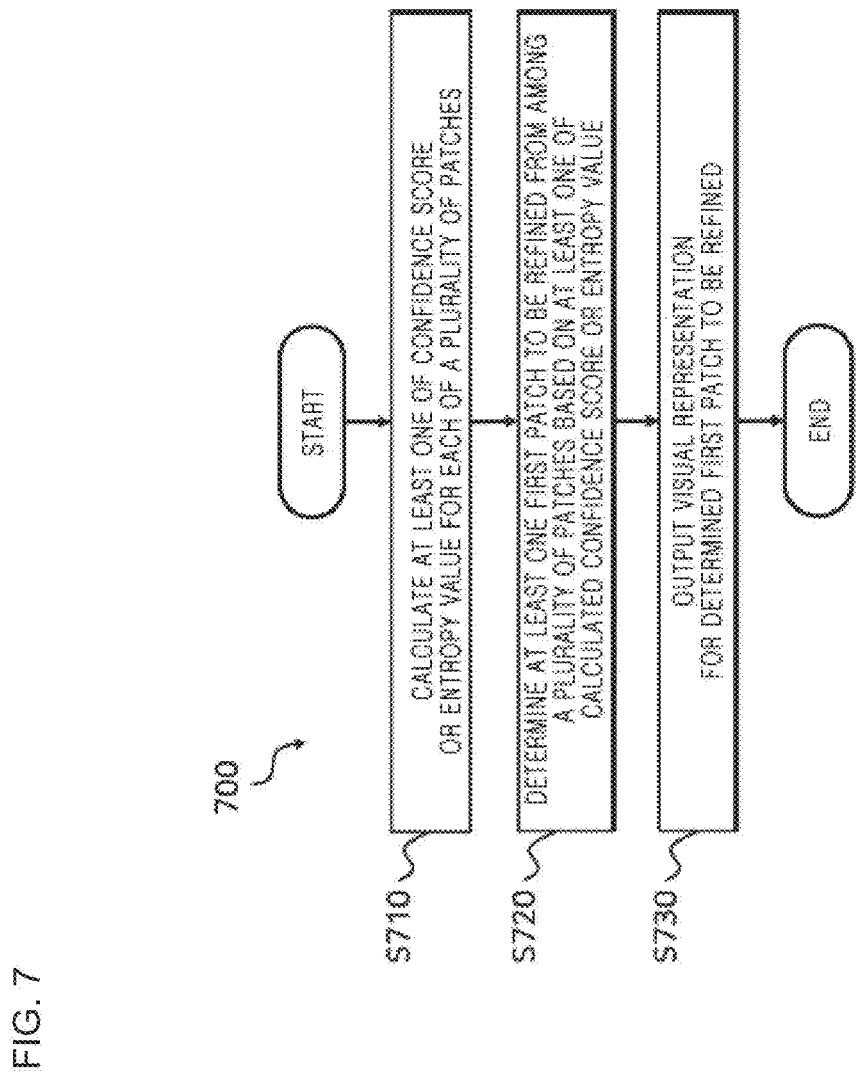
FIG. 7 is an exemplary flowchart illustrating a method for outputting a visual representation for a first patch to be refined according to an exemplary embodiment.

FIG. 7 is an exemplary flowchart illustrating a method for outputting a visual representation for the first patch to be refined according to an exemplary embodiment. According to an embodiment, the method 700 for outputting a visual representation for a patch to be refined may be performed by the information processing system (e.g., the information processing system 100). Additionally or alternatively, the method 700 may be performed by the annotator terminal (e.g., annotator terminal 110). As shown, the method 700 may begin at S710 in which the information processing system calculates at least one of a confidence score or an entropy value for each of a plurality of patches.

Then, at S720, the information processing system may determine at least one first patch to be refined from among the plurality of patches based on at least one of the calculated confidence score or the entropy value. According to an embodiment, when an entropy value related to a specific patch is high, the information processing system may determine the corresponding patch to be the first patch to be refined. In this case, the information processing system may determine whether or not to determine the specific patch to be the first patch to be refined, based on the entropy value associated with a class inferred for the specific patch. For example, when the entropy value associated with the class determined for the specific patch is greater than a predetermined entropy value, the specific patch may be determined to be the first patch to be refined.

Finally, at S730, the information processing system may output a visual representation for the determined first patch to be refined. For example, the information processing system may determine a visual representation for the determined first patch to be refined, and a pathology slide image applied with the visual representation for the first patch to be refined, or a part thereof may be provided to the annotator terminal.

Figure 8:
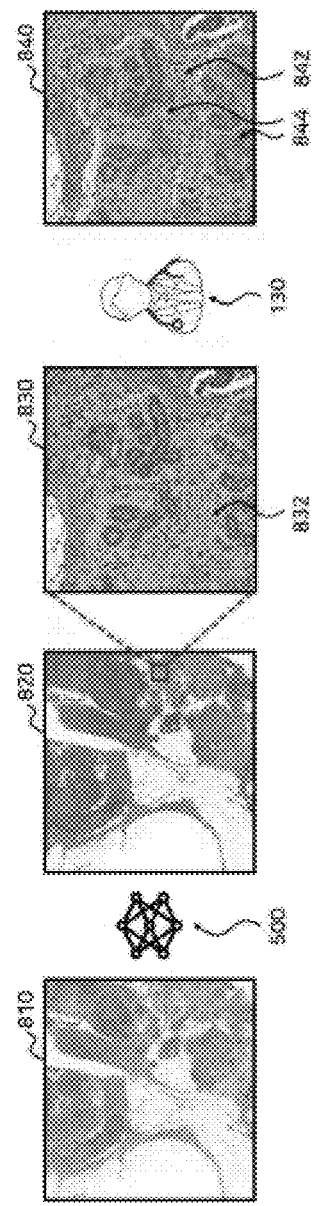
FIG. 8 is an exemplary diagram illustrating refinement of a label information item for a first patch to be refined according to an exemplary embodiment.

FIG. 8 is an exemplary diagram illustrating refinement of a label information item for the first patch to be refined according to an exemplary embodiment. The information processing system (e.g., the information processing system 100) may infer a plurality of label information items for a plurality of patches included in a pathology slide image 810 using a machine learning model. As shown, the plurality of label information items for the plurality of patches inferred as described above may be applied to the pathology slide image 810 to generate a pathology slide image 820. According to an embodiment, in the pathology slide image 820, a plurality of label information items for a plurality of inferred patches may be stored in association with a plurality of patches included in the pathology slide image 810. The pathology slide image 820 may be provided to the annotator 130 through the annotator terminal (e.g., the annotator terminal 110). In response to the annotator 130 selecting at least a certain area (e.g., a patch) of the pathology slide image 820, the information processing system may provide an enlarged image 830 of the selected at least certain area (e.g., the patch) to the annotator 130.

According to an embodiment, the information processing system 100 may be configured to calculate a confidence score and/or an entropy value of each of a plurality of patches associated with the label information item inferred by the machine learning model. For example, the information processing system 100 may calculate the confidence score for each of a plurality of classes corresponding to a plurality of patches. Then, based on the confidence score for each of the plurality of classes, an entropy value (e.g., uncertainty level, and the like) may be calculated for each class for the corresponding patch. The confidence score and/or the entropy value calculated as described above may be applied to the corresponding pathology slide image. For example, as shown, a visual representation for a plurality of patches may be output on each of the pathology slide image 820 and the enlarged image 830, indicating an area where the class is inferred and/or an area where the inferred class is uncertain, for a plurality of patches.

According to an embodiment, the information processing system 100 may be configured to determine at least one first patch 832 to be refined among a plurality of patches, based on at least one of the confidence score or the entropy value for each of the plurality of patches. In an example, the plurality of label information for the plurality of patches may include information (here, a plurality of classes, a confidence score for each class, an entropy value for each class, and the like) on a plurality of classes associated with the plurality of patches. For example, the first patch to be refined may refer to a patch having the highest confidence score for a class, but it may refer to a patch having a high entropy value. As another example, the first patch to be refined may refer to a patch having a low confidence score for a class. The first patch 832 to be refined may be provided to the annotator terminal 110 as a visual representation. For example, as shown, an area corresponding to the first patch 832 to be refined may be displayed in green.

In the label information inferred by the machine learning model through the annotator terminal 110, the annotator 130 may check at least one patch that may be determined to be of the uncertain inferred label information, and provide refined label information. According to an embodiment, the annotator 130 may provide the refined label information for the first patch 832 to be refined in the enlarged image 830. Accordingly, an image 840 including the refined label information may be generated and provided to the annotator 130 through the annotator terminal. For example, the first patch 832 to be refined, which is determined to be the uncertain area by the artificial neural network model 500 of the information processing system, may be refined by the annotator, and divided into and displayed as a first area 842 tagged with the cancer stroma label information and a second area 844 tagged with the cancer epithelium label information.

Figure 9:
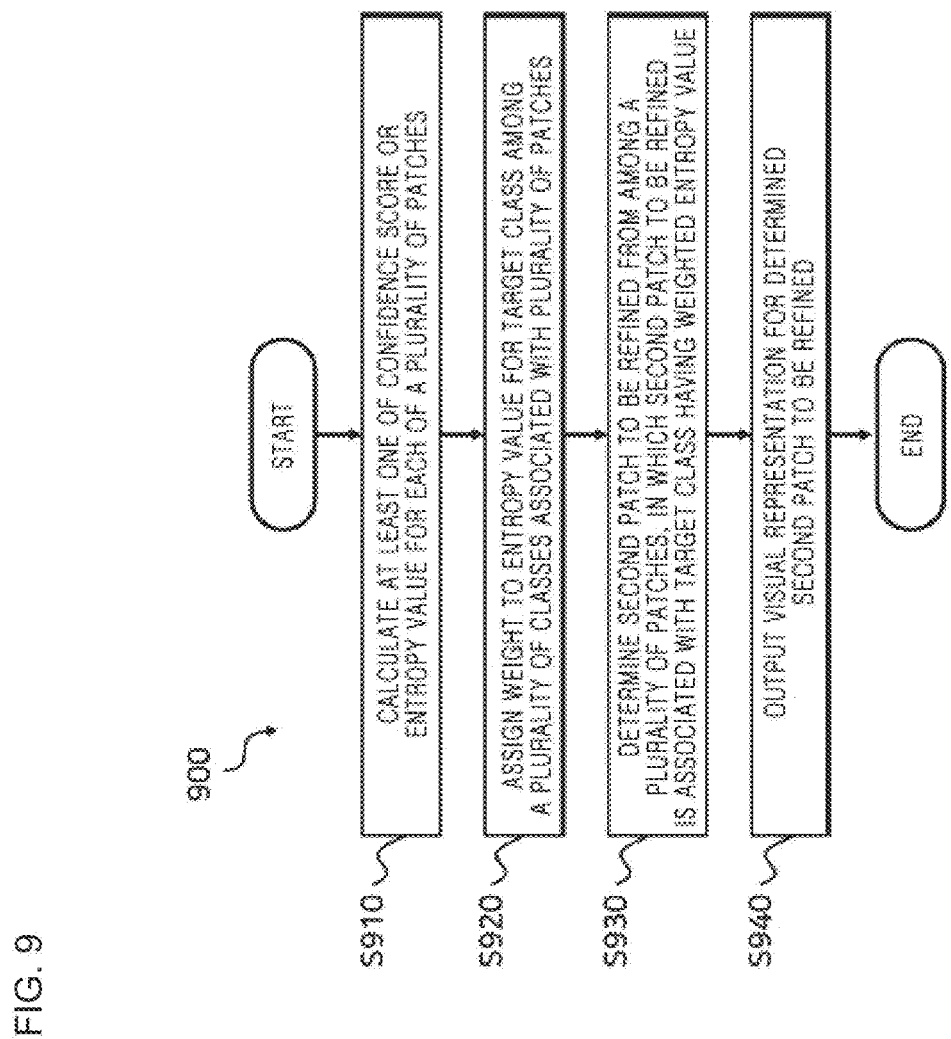
FIG. 9 is an exemplary flowchart illustrating a method for outputting a visual representation for a second patch to be refined according to an exemplary embodiment.

FIG. 9 is an exemplary flowchart illustrating a method for outputting a visual representation for a second patch to be refined according to an exemplary embodiment. According to an embodiment, the method 900 for outputting a visual representation for a patch to be refined may be performed by the information processing system (e.g., the information processing system 100). Additionally or alternatively, the method 900 may be performed by the annotator terminal (e.g., annotator terminal 110). As shown, the method 900 may begin at S910 of calculating at least one of a confidence score or an entropy value for each of a plurality of patches. In an example, the plurality of label information items for the plurality of patches may include a plurality of classes associated with the plurality of patches.

Then, at S920, the information processing system may assign a weight to an entropy value for a target class among a plurality of classes associated with the plurality of patches. In an embodiment, the information processing system may calculate the entropy value for each of a plurality of classes associated with a plurality of patches, and may assign a weight to the entropy value for the target class. This target class may be predetermined by the annotator.

Accordingly, at S930, the information processing system may determine, from among the plurality of patches, a second patch to be refined which is associated with the target class having the weighted entropy value. Then, at S940, the information processing system may output a visual representation for the determined second patch to be refined. For example, the information processing system may display the visual representation of the determined second patch to be refined on the pathology slide image including the patch or on a part of the pathology slide image including the patch. The pathology slide image or the part of the pathology slide image displayed as described above may be provided to the information processing system.

Figure 10:
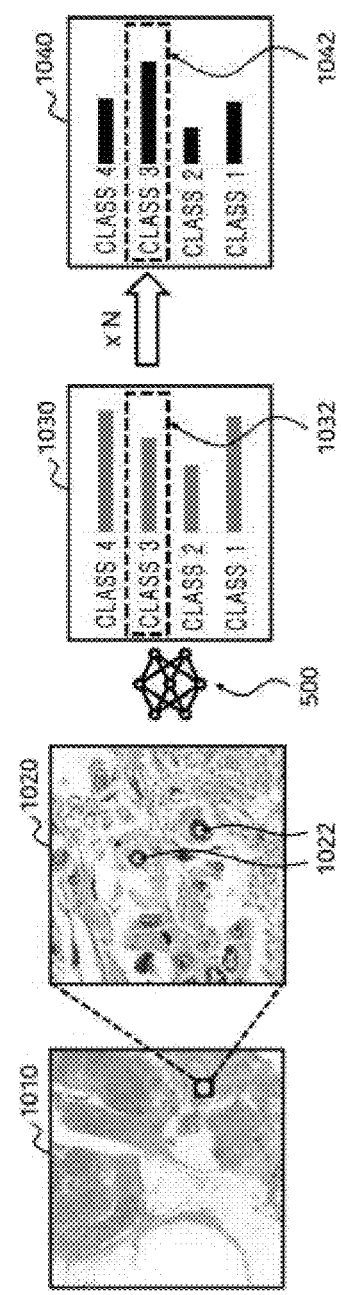
FIG. 10 is an exemplary diagram illustrating a method for assigning a weight to an entropy value for a target class according to an exemplary embodiment.

FIG. 10 is an exemplary diagram illustrating a method for assigning a weight to an entropy value for a target class according to an exemplary embodiment. As shown, in the pathology slide image 1010, a label information item for at least one patch included in the pathology slide image 1010 may be inferred by the artificial neural network model 500. In an example, the label information item may include a class, a confidence score of the class, and/or an entropy value for each class.

According to an embodiment, the information processing system (e.g., the information processing system 100) may be configured to assign a weight to the entropy value for the target class among a plurality of classes associated with a plurality of patches to determine at least one second patch to be refined associated with the weighted target class. For example, the information processing system may assign a weight to the entropy for a target class (e.g., macrophage, and the like) among a plurality of classes, in which the target class can be determined to be with uncertain inferred label information (that is, expected to be of a lower inference performance of the artificial neural network model 500) by the annotator (e.g., the annotator 130) through the annotator terminal (e.g., the annotator terminal 110), and determine a patch associated with the target class to be the second patch to be refined.

An entropy value 1030 for each class may be calculated using each class of a plurality of patches and a confidence score for each class. As shown, a target class 1032 has a lower entropy value than the other classes (e.g., class 1 and class 4) included in the entropy value 1030. Accordingly, the target class 1032 may not be determined to be the second patch to be refined by the information processing system. According to an embodiment, the information processing system may assign a weight to the entropy value for the target class among a plurality of classes associated with a plurality of patches. For example, the information processing system may assign a weight only to the target class 1032 among a plurality of classes included in the entropy value 1030 and extract a weighted entropy value 1040.

As shown, the weighted target class 1042 has a higher entropy value than the other classes included in the weighted entropy value 1040. Accordingly, the target class 1042 has the highest entropy value and may be determined to be the second patch to be refined by the information processing system. In addition, the target class 1042 determined to be the second patch to be refined is also applied when a plurality of label information items are applied to the pathology slide image, so that a visual representation of the target class 1042 may be output on the pathology slide image.

The second patch to be refined, which is determined as described above, may be provided to the annotator terminal as a visual representation. For example, a portion displayed in yellow in the pathology slide image 1010 may be associated with the second patch to be refined. In addition, a portion displayed in yellow on a pathology slide image 1010 may be associated with the second patch to be refined.

When the portion displayed in yellow included in the pathology slide image 1010 is selected, the information processing system may provide the enlarged image 1020 for at least certain area (e.g., a patch) of the pathology slide image 1010. Further, the enlarged image 1020 may include a plurality of patches 1022 associated with the target class. The annotator may provide through the annotator terminal a response to the second patch to be refined, among the label information inferred by the artificial neural network model 500. For example, the annotator may provide the refined label information for the second patch to be refined.

Figure 11:
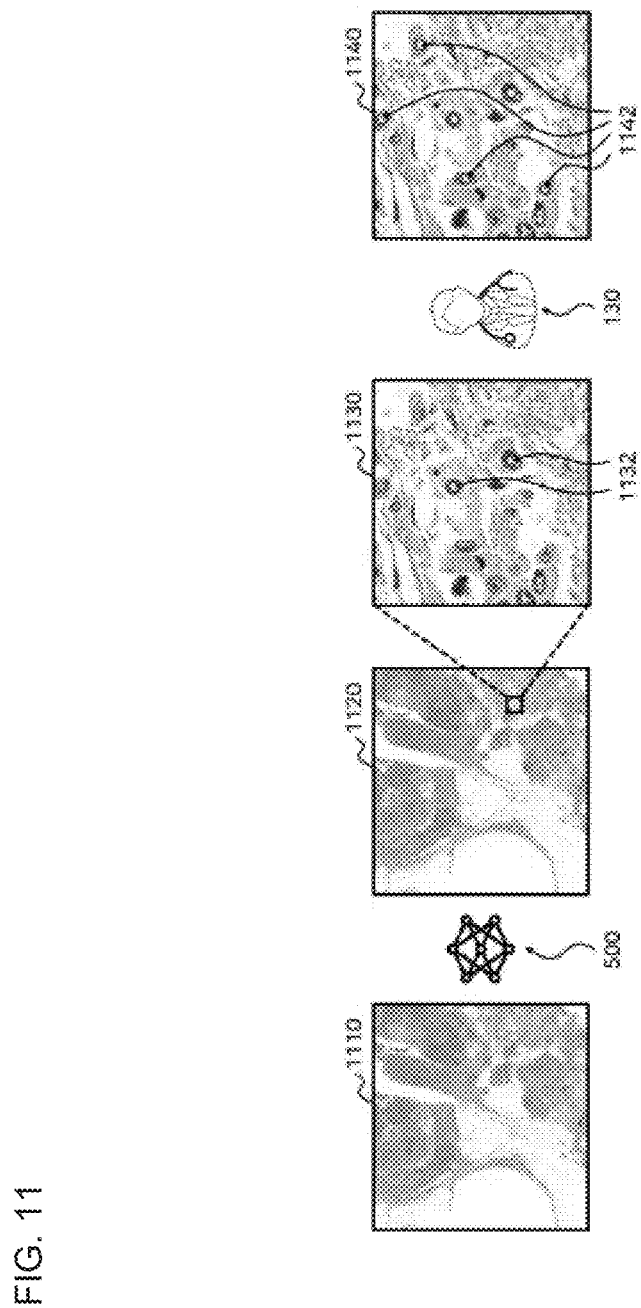
FIG. 11 is an exemplary diagram illustrating refinement of a label information item for a first patch to be refined according to an exemplary embodiment.

FIG. 11 is an exemplary diagram illustrating refinement of the label information item for the first patch to be refined according to an exemplary embodiment. As shown, the information processing system (e.g., the information processing system 100) may generate the label information item for at least one patch included in a pathology slide image 1110 using the artificial neural network model 500. The pathology slide image 1120 either including the generated information item or associated with the generated information item may be generated. At the request of the annotator terminal (e.g., the annotator terminal 110), the information processing system may provide an enlarged image 1130 for the area displayed in yellow (e.g., the patch associated with the target class) in the pathology slide image 1120.

The enlarged image 1130 may include a plurality of patches 1132 associated with the target class. In this example, the target class may be associated with lymphocytes. In addition, the plurality of patches 1132 associated with the target class are displayed by yellow circles, but are not limited thereto, and may be expressed in various visual representations such as areas, figures, different colors, or texts. In addition, all or at least part of the colored area may correspond to one or more patches. For example, the target class may be included in at least one label information item inferred by the artificial neural network model 500. The artificial neural network model 500 may not be able to infer all lymphocytes in the enlarged image 1130. Alternatively, the patch inferred as lymphocytes may not be actual lymphocytes.

The enlarged image 1130 may be refined by the annotator (e.g., the annotator 130) using the annotator terminal, and an image 1140 including the refined label information item may be generated. According to an embodiment, the information processing system may receive refined label information for at least one of the plurality of patches 1132 associated with the target class from the annotator terminal. In another embodiment, the information processing system may receive the refined label information items for a plurality of patches 1142 determined to be not associated with the target class from the annotator terminal. In this case, the refined label information item may be associated with the target class, and accordingly, the plurality of patches 1142 included in the image 1140 may be displayed in yellow.

Figure 12:
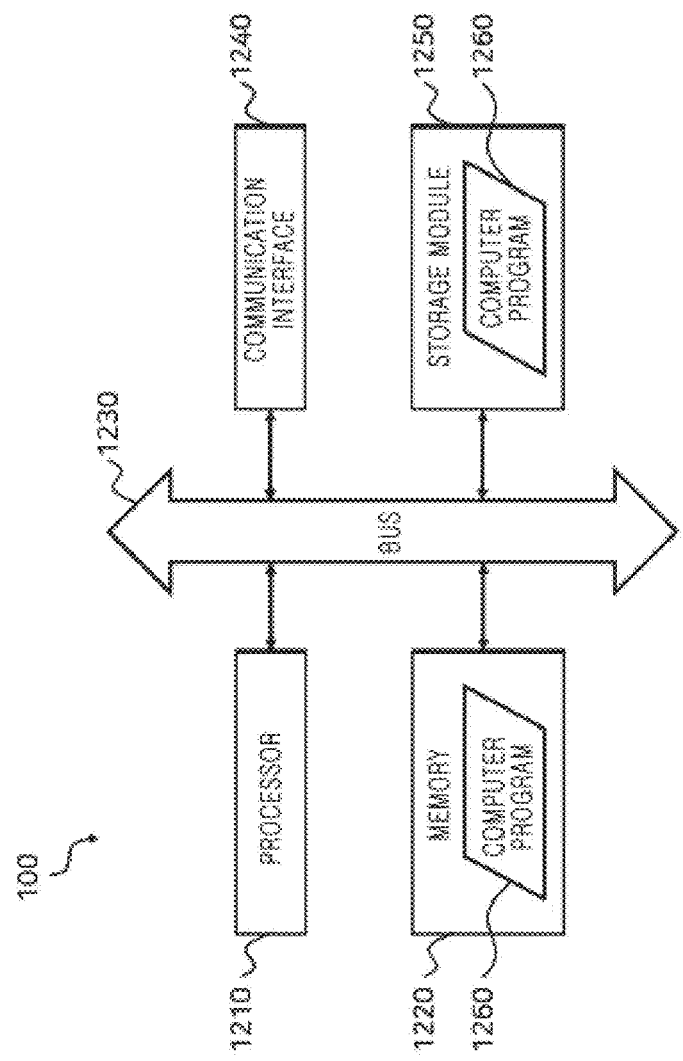
FIG. 12 is an exemplary configuration diagram illustrating a system for refining a label information item according to an exemplary embodiment.

FIG. 12 is an exemplary configuration diagram illustrating a system for refining a label information item according to an exemplary embodiment. As shown, the information processing system 100 may include one or more processors 1210, a bus 1230, a communication interface 1240, a memory 1220 that loads a computer program 1260 executable by the processor 1210, and a storage module 1250 that stores the computer program 1260. However, FIG. 12 shows only certain components related to the embodiment of the present disclosure. Accordingly, those of ordinary skill in the art to which the present disclosure pertains will be able to recognize that other general-purpose components may be further included in addition to the components shown in FIG. 12.

The processor 1210 controls the overall operation of components of the information processing system 100. The processor 1210 may include Central Processing Unit (CPU), Micro Processor Unit (MPU), Micro Controller Unit (MCU), Graphic Processing Unit (GPU), or any type of processor well known in the technical field of the present disclosure. In addition, the processor 1210 may execute an arithmetic operation on at least one application or program for executing the method according to the embodiments of the present disclosure. The information processing system 100 may include one or more processors.

The memory 1220 may store various types of data, instructions, and/or information. The memory 1220 may load one or more computer programs 1260 from the storage module 1250 in order to execute a method/operation according to various embodiments of the present disclosure. The memory 1220 may be implemented as a volatile memory such as RAM, although the technical scope of the present disclosure is not limited thereto.

The bus 1230 may provide a communication function between components of the information processing system 100. The bus 1230 may be implemented as various types of buses such as an address bus, a data bus, a control bus, or the like.

The communication interface 1240 may support wired/wireless Internet communication of the information processing system 100. In addition, the communication interface 1240 may support various communication methods other than Internet communication. To this end, the communication interface 1240 may be configured to include a communication module well known in the technical field of the present disclosure.

The storage module 1250 may non-temporarily store one or more computer programs 1260. The storage module 1250 may include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1260 may include one or more instructions that, when loaded into the memory 1220, cause the processor 1210 to perform an operation/method in accordance with various embodiments of the present disclosure. That is, the processor 1210 may perform operations/methods according to various embodiments of the present disclosure by executing one or more instructions.

For example, the computer program 1260 may include one or more instructions for causing operations of: obtaining information on the pathology slide image; obtaining the label information item for the pathology slide image and/or at least one patch included in the pathology slide image; training a machine learning model to infer a result (e.g., label information) for the pathology slide image and/or at least one patch included in the pathology slide image; inferring the label information for the pathology slide image and/or at least one patch included in the pathology slide image through the trained machine learning model; and refining the label information item for the pathology slide image and/or at least one patch included in the pathology slide image, to be performed. In this case, a system for refining a label information item according to some embodiments of the present disclosure may be implemented through the information processing system 100.

The above description of the present disclosure is provided to enable those skilled in the art to make or use the present disclosure. Various modifications of the disclosure will be readily apparent to those skilled in the art, and the generic principles defined herein may be applied to various modifications without departing from the spirit or scope of the disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A method for refining label information, performed by at least one computing device, the method comprising:
acquiring a pathology slide image including a plurality of patches;
inferring a plurality of label information items for the plurality of patches included in the acquired pathology slide image using a machine learning model;
applying the inferred plurality of label information items to the pathology slide image;
calculating at least one of a confidence score or an entropy value for each of the plurality of patches;
selecting at least one first patch to be refined from among the plurality of patches based on a comparison of at least one of the calculated confidence score or the entropy value and a predetermined value; and
providing the pathology slide image applied with the inferred plurality of label information items to an annotator terminal,
wherein the plurality of label information items for the plurality of patches includes a plurality of classes associated with the plurality of patches, and
the calculating at least one of the confidence score or the entropy value for each of the plurality of patches includes assigning a weight to the entropy value for a target class among the plurality of classes associated with the plurality of patches.

2. The method according to claim 1, further comprising receiving, from the annotator terminal, a response to at least one label information item among the plurality of inferred label information items, wherein the at least one label information item is associated with at least one patch among the plurality of patches.

3. The method according to claim 2, wherein the receiving, from the annotator terminal, the response to at least one label information item among the inferred plurality of label information items includes, when receiving a confirmation on the at least one label information item, classifying the at least one patch and the at least one label information item into a training dataset of the machine learning model.

4. The method according to claim 2, wherein the receiving, from the annotator terminal, the response to at least one label information item among the inferred plurality of label information items includes:
receiving a refined label information item for the at least one patch; and
classifying the at least one patch and the refined label information item into a training dataset of the machine learning model.

5. The method according to claim 4, wherein the classifying the at least one patch and the refined label information item into the training dataset of the machine learning model includes assigning a weight to the refined label information item for the at least one patch, which is used for training the machine learning model.

6. The method according to claim 4, wherein the providing the pathology slide image applied with the inferred plurality of label information items to the annotator terminal includes providing a compressed image of the pathology slide image to the annotator terminal, wherein the compressed image is associated with compressed label information items of the plurality of label information items, and
the receiving the refined label information item for the at least one patch includes:
receiving, from the annotator terminal, a request for the at least one label information item corresponding to a first compressed label information item selected from the compressed image;
providing the at least one label information item to the annotator terminal; and
receiving a refined label information item for the provided at least one label information item.

7. The method according to claim 1, wherein the applying the inferred plurality of label information items to the pathology slide image includes outputting a visual representation of the determined at least one first patch to be refined.

8. The method according to claim 7, wherein the visual representation indicates an area where the label information item for the selected at least one first patch is uncertain.

9. The method according to claim 1, wherein the determining at least one patch to be refined from among the plurality of patches includes determining, from among the plurality of patches, at least one second patch to be refined, which is associated with the target class having the weighted entropy value, and
the applying the inferred plurality of label information items to the pathology slide image includes outputting a visual representation of the determined at least one second patch to be refined.

10. An information processing system comprising:
a memory storing one or more instructions; and
a processor configured to, by executing of the stored one or more instructions:
acquire a pathology slide image including a plurality of patches;
infer a plurality of label information items for the plurality of patches included in the acquired pathology slide image using a machine learning model;
apply the inferred plurality of label information items to the pathology slide image;
calculate at least one of a confidence score or an entropy value for each of the plurality of patches;
select at least one first patch to be refined from among the plurality of patches based on a comparison of at least one of the calculated confidence score or the entropy value and a predetermined value; and
provide the pathology slide image applied with the inferred plurality of label information items to an annotator terminal
wherein the plurality of label information items for the plurality of patches includes a plurality of classes associated with the plurality of patches, and
the processor is further configured to assign a weight to the entropy value for a target class among the plurality of classes associated with the plurality of patches.

11. The information processing system according to claim 10, wherein the processor is further configured to receive, from the annotator terminal, a response to at least one label information item among the inferred plurality of label information items, and
the at least one label information item is associated with at least one patch among the plurality of patches.

12. The information processing system according to claim 11, wherein the processor is further configured to, when receiving a confirmation on the at least one label information item, classify the at least one patch and the at least one label information item into a training dataset of the machine learning model.

13. The information processing system according to claim 11, wherein the processor is further configured to:
receive a refined label information item for the at least one patch; and
classify the at least one patch and the refined label information item into a training dataset of the machine learning model.

14. The information processing system according to claim 13, wherein the processor is further configured to assign a weight to the refined label information item for the at least one patch, which is used for training the machine learning model.

15. The information processing system according to claim 13, wherein the processor is further configured to:
provide a compressed image of the pathology slide image to the annotator terminal;
receive, from the annotator terminal, a request for the at least one label information item corresponding to a first compressed label information item selected from the image;
provide the at least one label information item to the annotator terminal; and
receive a refined label information item for the provided at least one label information item.

16. The information processing system according to claim 10, wherein the processor is further configured to output a visual representation of the determined at least one first patch to be refined.

17. The information processing system according to claim 16, wherein the visual representation indicates an area where the label information item for the selected at least one first patch is uncertain.

18. The information processing system according to claim 10, wherein the processor is further configured to:
determine, from among the plurality of patches, at least one second patch to be refined, which is associated with the target class having the weighted entropy value; and
output a visual representation of the determined at least one second patch to be refined.

* * * * *